United States Patent [19]

Marshall et al.

[11] Patent Number: 5,304,638
[45] Date of Patent: Apr. 19, 1994

[54] PROTEIN SEPARATION MEDIUM

[75] Inventors: Philip J. Marshall, Huntingdon; Christopher R. Lowe, Saffron Walden, both of England

[73] Assignee: Central Blood Laboratories Authority, Elstree, England

[21] Appl. No.: 777,531

[22] PCT Filed: Jun. 8, 1990

[86] PCT No.: PCT/EP90/00910
§ 371 Date: Dec. 4, 1991
§ 102(e) Date: Dec. 4, 1991

[87] PCT Pub. No.: WO90/14886
PCT Pub. Date: Dec. 13, 1990

[30] Foreign Application Priority Data

Jun. 8, 1989 [GB] United Kingdom ............... 8913183

[51] Int. Cl.⁵ .................. A61K 35/14; B01D 15/08
[52] U.S. Cl. .................................. 530/383; 530/364; 530/416; 530/417; 210/263; 210/635; 210/656; 210/660; 210/661; 210/666; 210/683; 210/685; 210/702; 210/724; 210/734; 210/736
[58] Field of Search ............... 530/383, 364, 389, 391, 530/416, 417; 210/263, 635, 656, 660, 661, 666, 683, 685, 702, 724, 734, 736

[56] References Cited

U.S. PATENT DOCUMENTS

| | | | |
|---|---|---|---|
| 3,860,573 | 1/1975 | Honkanen et al. | 530/417 |
| 4,157,431 | 6/1979 | Fields et al. | 526/15 |
| 4,397,841 | 8/1983 | Johnson | 424/101 |
| 4,471,112 | 9/1984 | Johnson | 536/21 |
| 4,508,709 | 4/1985 | Amphlett | 424/101 |
| 4,675,384 | 6/1987 | Dromard et al. | 530/364 |
| 4,883,598 | 11/1989 | Riethorst et al. | 210/656 |

OTHER PUBLICATIONS

Clark, Jr. et al, *Experimental Biochemistry*, second edition, W. H. Freeman and Company, San Francisco, 1977, pp. 15–20.
Morgenthaler, *Thromb. Haemostas.*, 47:124–127 (1982).
Neal et al, *Thromb. Haemostas.*, 54:78 (1985).
Tuddenham et al, *British Journal of Haematology*, 52:259–267 (1982).
Austen, *British Journal of Haematology*, 43:669–674 (1979).
Austen et al, *Thromb. Haemostas.*, 48:46–48 (1982).

*Primary Examiner*—Michael G. Wityshyn
*Assistant Examiner*—Abdel A. Mohamed
*Attorney, Agent, or Firm*—Burns, Doane, Swecker & Mathis

[57] ABSTRACT

A separation medium for use in protein separation comprising a water-insoluble matrix carrying a plurality of polyamine groupings, the polyamine groupings having at least three basic nitrogen atoms, the basic nitrogen atoms being separated from each other by a chain of at least two intervening carbon atoms, there being a total of 5 such intervening carbon atoms when there is a total of three nitrogen atoms in each polyamine group, which may be used for at least partially purifying factor VIII.

23 Claims, 1 Drawing Sheet

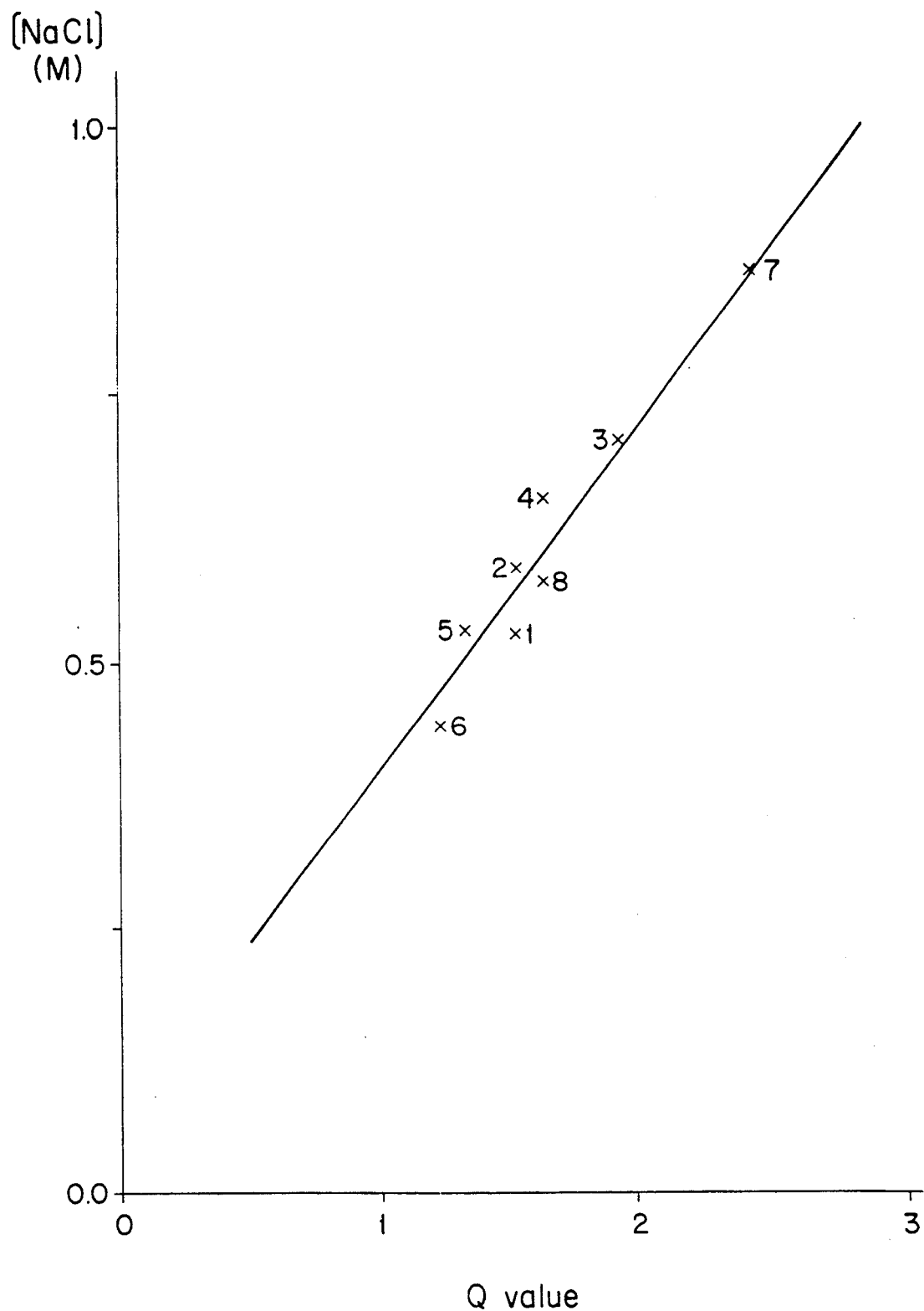

PROTEIN SEPARATION MEDIUM

BACKGROUND OF THE INVENTION

1. Field of the Invention

This invention relates to improved media for the separation of blood coagulation factors from plasma concentrates and methods of separation and isolation using these media.

DESCRIPTION OF THE RELATED ART

Blood Coagulation Factor VIII (abbreviated herein to factor VIII) is a protein component of blood, the absence or deficiency of which results in haemophilia. It is obtained from donated blood plasma in many countries on an industrial scale for administration to haemophiliacs. Factor VIII is present in plasma at very low concentrations and current processes attempt to produce purified factor VIII-containing products in which the specific activity of the factor VIII has been significantly increased relative to other plasma proteins. In general factor VIII is isolated in the form of a complex, the complex being formed with von Willebrand Factor (vWF).

One method of purification of factor VIII which has been employed is adsorption onto and elution from a separation medium having an affinity for factor VIII. In that the affinity of the medium for other proteins is normally different from that for factor VIII, some separation may be achieved, particularly using chromatographic techniques.

It is important in such separation techniques that the separation medium not only shows some selectivity in the adsorption of factor VIII but also that large amounts of factor VIII can be adsorbed per unit volume of separation medium and can be eluted at a high rate of recovery Hitherto, such separation media for factor VIII have consisted of an inert substrate such as an agarose, e.g. Sepharose, carrying functional groupings having an affinity for factor VIII, notably aminoalkyl groups. Typical materials of this type have been described by Austen DEG (1979: Br. J.Haematol. 43, 669–674); Austen DEG and Smith JK (1982: Thromb.Haemostas. 48, 46–48) and U.S. Pat. No. 4,508,709.

In particular, Neal G.G. et al have described in a Poster presentation in San Diego in July 1985 certain separation media for factor VIII comprising Sepharose bound to a wide range of amines including certain polyamines. (Neal GG, Smith JK and Hersee D, 1985, Thromb.Haemostas. 54, 78 Conference Abstract). The polyamines showed better absorption of factor VIII than the simple monoamines but alkylenediamines gave better results than dialkylenetriamines such as diethylenetriamine or di(n-propylene)-triamine.

BRIEF DESCRIPTION OF THE DRAWING

FIG. 1 is a graph illustrating the linear relationship between Q value and sodium chloride concentration required to elute Factor VIII from various polyamine ligands attached to sepharose.

Our further investigations have revealed that higher polyamine groups are capable of giving better results in isolation of factor VIII than the amine groups described by Neal et al, and that furthermore, a high number of protonated amino groups relative to the number of methylene groups is important in determining the selectivity for factor VIII. We have found, in this context, that the polyamine having the formula $H_2N(CH_2)_2NH(CH_2)_3NH_2)$ (N-(2-aminoethyl)-1,3-propanediamine) gave better results than either $H_2N(CH_2)_2NH(CH_2)_2NH_2$ (diethylenetriamine) or $H_2N(CH_2)_3NH(CH_2)_3NH_2$ (di(n-propylene) triamine), and polyamines having four or more nitrogen atoms, such as triethylenetetramine (TETA), gave even better results. In the case of diethylenetriamine, the proximity of the nitrogens prevents full protonation of all three at appropriate pH levels e.g. pH 5.5, whereas the introduction of one further methylene group, to give the compound $H_2N(CH_2)_2NH(CH_2)_3NH_2$ allows full protonation at pH 5.5.

According to the present invention therefore we provide a separation medium for use in protein separation comprising a water-insoluble matrix carrying a plurality of polyamine groupings, said polyamine groupings having at least 3 basic nitrogen atoms, said basic nitrogen atoms being separated from each other by a chain of at least two intervening carbon atoms, there being a total of 5 such intervening carbon atoms when there is a total of three nitrogen atoms in each polyamine group.

The polyamine groups each preferably contain at least four nitrogen atoms.

The polyamine groups may each be straight or branched chain or monocyclic or polycyclic groupings. The nitrogen atoms may be provided by amino groups attached to a continuous chain of carbon atoms, as in polyvinylamines or polyallylamines, or interrupt the carbon chains as in polyalkylene polyamine groups such as in triethylenetetramine and polyethyleneimine. Syntheses of such groupings show some tendency to produce ring structures and at least some of the polyamine groupings may be monocyclic, wherein all or part of a polyalkylenepolyamine grouping has formed a single ring containing two or more nitrogens, or where there are several such rings linked by intervening carbon atoms or carbon and nitrogen atoms.

The polyalkylene polyamine groups attached to the matrix may be the same or different.

The intervening carbon atoms between pairs of nitrogen atoms, (i.e. the chain of carbon atoms directly linking the nitrogen atoms, exclusive of side chains or substituents) may in general consist of or form part of a straight or branched alkylene or cycloalkylene grouping. Alkylene groups are preferred. The number of intervening carbon atoms between pairs of nitrogen atoms is preferably not more than 3. It will be appreciated that where a polyalkylenepolyamine group contains cyclised groups containing two nitrogen atoms, there will be two sets of intervening carbon atoms, for example, as in a group

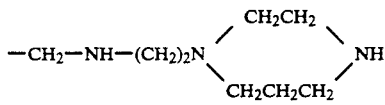

The polyalkylenepolyamine group may also be branched, that is the linear polyalkylenepolyamine chain may carry amino, alkyl, aminoalkyl or polyalkylenepolyamine side groups which may themselves be branched, and which may be attached to either carbon or nitrogen atoms in the linear chain.

The carbon atoms in the polyamine grouping may carry other substituent non-acidic groups, such as hydroxyl or oxo groups The nitrogen atoms may be contained in primary, secondary, tertiary or quaternary amine groups. Thus, for example, nitrogen atoms in secondary, tertiary and quaternary amine groups may carry alkyl substituents, e.g. having 1-3 carbon atoms, in addition to intervening carbon chains joined to other nitrogen atoms. There is, however, preferably at least one terminal primary amine group and, in general, the nitrogen atoms preferably carry at least one hydrogen atom.

The most preferred polyamine groups are linear polyalkylene polyamine groups having 2 to 5 carbon atoms in the alkylene groups, more preferably 2 or 3 carbon atoms. Particularly good results have been obtained using polyamine groups in which ethylene and n-propylene groups alternate since this combines good protonation with a good nitrogen-carbon ratio. Such polyamine groups may be represented by the formula:

$$-NH-[(CH)_2NH(CH_2)_3NH]_m-(CH_2)_2NH_2$$

where m is an integer.

The water-insoluble matrix will normally be an organic matrix e.g. a polymeric substance such as agarose carrying functional groups such as hydroxyl which may be used to attach the required polyamine groupings using coupling agents such as cyanogen bromide, epichlorohydrin, carbonyl diimidazole or 1,4-butanediol diglycidyl ether. Such coupling agents will thus contribute a linking group which forms the initial section of the polyamine group. This is preferably an alkylene group having 1 to 10 carbon atoms which may be interrupted with oxygen atoms and may carry substituents such as hydroxyl or oxo groups. The carbonyl linking group of the carbamate grouping formed by coupling with carbonyl diimidazole can be regarded as a methylene group carrying an oxo substituent.

Particularly preferred polyamine groups for use in media according to the invention include:

TABLE 1

| | |
|---|---|
| $-L-NH(CH_2)_2NH(CH_2)_3NH_2$ | (A) |
| $-L-NH(CH_2)_2NH(CH_2)_2NH(CH_2)_2NH_2$ | (B) |
| $-L-NH(CH_2)_2NH(CH_2)_3NH(CH_2)_2NH_2$ | (C) |
| $-L-NH(CH_2)_3NH(CH_2)_2NH(CH_2)_3NH_2$ | (D) |
| $-L-NH(CH_2)_3NH(CH_2)_3NH(CH_2)_3NH_2$ | (E) |
| $-L-NH(CH_2)_2NH(CH_2)_2NH(CH_2)_2NH(CH_2)_2NH_2$ | (F) |
| $-L-NH(CH_2)_2NH(CH_2)_3NH(CH_2)_2NH(CH_2)_3NH(CH_2)_2NH_2$ | (G) |
| $-L-NH(CH_2)_2NH(CH_2)_2NH(CH_2)_2NH(CH_2)_2NH(CH_2)_2NH_2$ | (H) |

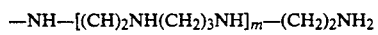

$$-L-NH(CH_2)_3N\underset{CH_2CH_2}{\overset{CH_2CH_2}{\diagup\!\!\!\diagdown}}N(CH_2)_3NH_2 \quad (I)$$

where L is a linking group as described above.

Preferred polyamine groups are (B) and (G) above.

The matrix carrying the polyamine groups is preferably a polymeric hydrophilic material, which may be of natural origin such as agarose or cellulose or dextran (which may be cross-linked) or may be a synthetic polymer such as polyacrylamide or a copolymer of oligoethyleneglycol, glycidylmethacrylate and pentaerythroldimethacrylate. The matrix may also be an inorganic material such as macroporous silica. The matrix is preferably in the form of an aqueous gel. Preferred matrix materials include those having the commercial names of Sepharose, Sephadex, Sephacryl, Fractogel and Trisacryl.

The separation media of the invention are advantageously prepared by coupling an appropriate polyamine to a water-insoluble matrix. As indicated above coupling will normally be effected using a coupling agent which will be a di-functional molecule, preferably having 1-10 carbon atoms, for example, epichlorohydrin (L=-CH$_2$CH(OH)-CH$_2$-), carbonyl diimidazole (L=—CO—) or 1,4-butanediol diglycidylether (L=—CH$_2$CH(OH)CH$_2$—O—(CH$_2$)$_4$—O—CH$_2$—CH(OH)—CH$_2$—). Such reagents will couple to hydroxyl, amino or sulphydryl groups on the matrix.

The loading of ligand on the matrix will generally be in the range 10 to 90, preferably 20 to 60, micromoles per ml of gel.

Many of the polyamines for use in preparing the separation media of the invention are commercially available. In general, they may be synthesised by reaction of available shorter polyamines such as ethylene diamine with difunctional alkanes such as ethylene or propylene dibromide. Where such reactions give mixtures, for example cyclic products, such side-products may be removed by fractionation or may often simply be left in the mixture and reacted with the activated matrix to produce a product of the invention having mixed polyamine groups.

As indicated above, our studies have shown that for good results in terms of increased specific activity of factor VIII, the immobilised polyamine should have a high ratio of protonated to unprotonated nitrogen atoms at pH 5.5 (the optimal pH for factor VIII purification and avoidance of protein precipitation) and a high ratio of nitrogen to carbon atoms.

For the polyamines that we have so far investigated we have been able to derive an empirical function Q, defined as:

$$Q=1.0n_1N^+ +0.3n_2N-0.3n_3C$$

where $n_1N^+$ is the number of protonated nitrogens and $n_2N$ is the number of unprotonated nitrogens at pH 5.5 (estimated from experimentally determined pKa values: Critical Stability Constants, Volume 2: Amines by Smith, R.M. and Martell, A.E., Plenum Press, New York and London, 1975) and $n_3C$ is the total of intervening carbon atoms.

The selectivity of the groups in Table 1 appears to be related to Q as the calculated value of Q appears to correlate in a qualitative sense with the purity of the eluted factor VIII fraction in terms of the relative absence of contaminant proteins. Table 4 hereinafter lists Q values and a score related to the separation of factor VIII activity from the contaminant proteins. In general, it is preferable to use a ligand whose calculated Q is at least 1.5.

Furthermore, the chromatographic properties of the ligands towards factor VIII may be changed by altering their chemical structure for example by transition metal binding e.g. with $Cu^{2+}$ or chemical reaction, e.g. N-alkylation. Thus, for example, alkylation can be effected by reaction of the ligand carried on the separation medium with an alkylating agent, for example an alkyl halide such as methyliodide.

According to a further aspect of the invention, we provide a method of at least partially purifying factor VIII comprising loading a factor VIII-containing material onto a separation medium according to the invention followed by washing and eluting with an increasing electrolyte concentration.

The separation media according to the invention will normally be used in columns using essentially chromatographic techniques. Thus, the media will normally be packed into columns and equilibrated with an appropriate buffer at a pH in the range 5.0 to 8.0, most preferably at pH 5.0 to 6.0, pH 5.5 being optimal. A useful buffer is acetate buffer, e.g. 100 mM acetic acid, pH adjusted to 5.5 with sodium hydroxide. Lysine hydrochloride at e.g. 100 mM, a polyalcohol such as glycerol at e.g 10% v/v and calcium ions at e.g. 10 mM may usefully be included in the buffer Other useful buffers are Bis-Tris buffer, e.g. 100 mM Bis-Tris pH 6.0-6.5 and Tris buffer, e.g. 100 mM Tris pH 7-8. The buffer may also contain sodium chloride at up to 1.0 M, depending on the ligand.

The factor VIII containing material for separation will then be loaded onto the column; where solid it will usually be dissolved in a suitable buffer, preferably the buffer used to equilibrate the column. Alternatively, the separation medium may be mixed with the buffer-equilibrated factor VIII containing material for a period in a batch-wise fashion, collected by centrifugation, and poured into a column followed by chromatographic elution This technique is especially useful if the factor VIII containing material is of low potency, such as plasma. When the factor VIII containing material is plasma, it may be buffer exchanged into an appropriate buffer, e.g. sodium chloride, using for example Sephadex, e.g. Sephadex G25.It may also be pretreated to remove certain contaminating proteins, for example prothrombin, by treatment with an adsorbent e.g. DEAE-Sephadex.

Loading is desirably followed by washing with the buffer used to equilibrate the column.

Development of the column may be effected with solutions of increasing concentration of electrolyte in a buffer of the kind used for equilibration. The electrolyte is conveniently sodium chloride, but other salts may be used, e.g. ammonium chloride, sodium sulphate, ammonium sulphate, trisodium citrate together with calcium chloride. Either a concentration gradient or stepwise increases in concentration may be used. When stepwise increases in electrolyte concentration are used, a low concentration of electrolyte is used initially to remove bound proteins other than factor VIII, followed by a higher concentration to remove the factor VIII. The concentration of added electrolyte for elution of factor VIII may, for example, be varied between 0.2 and 4.0 M sodium chloride, depending on the ligand. Elution by increasing concentration gradient may be effected in more than one stage.

The factor VIII containing solution for separation may for example contain whole plasma, plasma pretreated to remove prothrombin, cryoprecipitate, intermediate purity concentrate (IPC), high purity concentrate-(HPC) or solutions of cryoprecipitate pre-treated to remove most of the fibrinogen, fibronectin and vitamin K-dependent clotting factors. These solutions may be treated with solvent-detergent systems, e.g. tri-n-butyl phosphate and Tween 80, for virus inactivation, and we have found that these materials do not influence the adsorption and elution of factor VIII.

Factor VIII will normally be present in such starting materials in association with von Willebrand factor (vWF) and may be separated in this form but with a generally increased ratio of factor VIII to vWF. The amounts of fibrinogen and fibronectin contaminating the factor VIII are diminished approximately 50-fold by this method. Purity of factor VIII may be increased by at least 50-fold by this method.

The following example and preparations are given by way of illustration and with reference to the accompanying drawing in which FIG. 1 shows the correlation between Q values and the NaCl concentrations required for elution of factor VIII from the various ligands and wherein the numbers by the points refer to the ligands numbered in Table 4.

Materials

Chemicals

Polyamine compounds were generally obtained from Aldrich, except pentaethylenehexamine which was from Fluka. Polyamines C and G (Table 1) were synthesised according to Van Alphen, J. (Recueil des Travaux Chimiques des Pays-Bas 55 835 (1936) and same journal 56 343 (1937)) and polyvinylamine was synthesised according to Dawson, D.J., Gless, R.D and Wingaard, R.E. (J. Am. Chem. Soc. 98 5996-6000 (1976)) using generally available reagents. Coupling agents were obtained from Sigma (1,4-butanediol diglycidyl ether and carbonyldiimidazole) and BDH (epichlorohydrin).

Supports

Sepharose, Sephadex and Sephacryl were obtained from Pharmacia. Trisacryl was obtained from IBF-LKB. Fractogel was obtained from BDH.

General Coupling Procedures

Carbonyldiimidazole (CDI)

The gel may be transferred to a non-aqueous environment by sequential washing with increasing concentrations of a suitable solvent, for example acetone, and finally with neat solvent.

A quantity of carbonyldiimidazole, for example 3.5 g per 100 ml of gel, is allowed to react with the gel at room temperature for 15 minutes The activated gel is then washed rapidly with a large amount of a solvent such as acetone, and then allowed to react for about 17 hours at ambient temperature with an aqueous solution of the polyamine compound The concentration of this solution is preferably about 10% v/v, and the pH is adjusted to between 9 and 11. The coupled gel may then be washed extensively with water, dilute acetic acid and finally water.

When the support to which the polyamine was being attached was Sephacryl S-500, the activation, wash and coupling steps were all carried out using dry acetone as solvent. Furthermore, the coupling step was carried out at 4° C.

Epichlorohydrin (ECH)

To 100 g of washed, suction dried gel, 200 mg of sodium borohydride is added, and 50 ml of 2 M sodium hydroxide solution. 6×5 ml aliquots of epichlorohydrin, and 6×10 ml aliquots of sodium hydroxide are added over 2 hours during which the gel is agitated at room temperature. The mixture is agitated for a further 15 hours, and then the gel is washed extensively with water.

The activated gel is then added to an equal volume of a solution containing about 10% of the polyamine compound and 0.1% of sodium borohydride dissolved in 2 M sodium carbonate solution, pH adjusted to about 11, and the mixture is agitated at 60° C. for about 20 hours. The gel is washed extensively with water, then aqueous acetic acid and finally water.

When the support to which the polyamine was being attached was Fractogel TSK HW-55, the following method was used. 100 g of washed suction dried gel is mixed with 60 ml of 9 M sodium hydroxide solution, 80 ml of water and 60 ml of ECH at a temperature of approximately 40° C. for 2 hours. The gel is collected by filtration, washed with water, and then mixed with 100 ml of a 10% solution of the polyamine in water at 60° C. for 3 hours. The gel is washed extensively with water, then aqueous acetic acid and finally water.

1,4-butanediol-diglycidyl ether (BDE)

Coupling using 1,4-butanediol-diglycidyl ether is essentially identical to that described for epichlorohydrin except that in the activation step the suction dried gel is mixed in one step with an equal volume of 0.6 M NaOH solution, and a similar volume of 1,4-butanediol diglycidyl ether.

Synthesis of ligands (C) and (G) (Table 1)

These ligands, having the structures $H_2N-(CH_2)_2-NH-(CH_2)_3-NH-(CH_2)_2-NH_2$ (C) and $H_2N-(CH_2)_2-NH-(CH_2)_3-NH-(CH_2)_2-NH-(CH_2)_3-NH-(CH_2)_2-NH_2$ (G) were synthesised according to Van Alphen, J. in Recueil des Travaux Chimiques des Pays-Bas 55 835 (1936) and by the same author, same journal 56 343 (1937). The experimental details are briefly as follows: 1,2-diaminoethane (45 ml, 0.67 mol) and absolute ethanol (40 ml) were placed in a 250 ml round bottomed flask, to which was attached a water cooled condenser and a pressure equalised dropping funnel containing 1,3-dibromopropane (12.5 ml, 0.124 mol). The contents of the flask were stirred magnetically and the 1,3-dibromopropane was added dropwise so as to maintain a gentle reflux. When addition was complete, the mixture was heated under reflux for 1 hour. The stirring was continued, and 35 g of potassium hydroxide was added, and the mixture was again heated under reflux for 30 minutes. Solid KBr was removed by filtration, and ethanol and 1,2-diaminoethane were removed by distillation. The residue was cooled to give a solid and a yellowish liquid which was decanted. The liquid was fractionated by distillation under reduced pressure (ca 18 mm Hg). Two fractions, having boiling ranges of 164°–166° C. and ca 208° C, (18 mm Hg) were collected. The first fraction was about twice the volume of the second, and both were pale yellow. The boiling point of the first fraction was within the range 280°–290° C. at normal pressure, which identifies it as being compound (C) By reference from Van Alphen's work the higher boiling fraction will be compound (G). A tar-like residue remained in the flask after the reduced pressure distillation.

Assays

1. Factor VIII assays were performed either by standard methods for the two-stage clotting assay, or by use of the Coatest factor VIII assay kit (Kabi) according to the method of Prowse, C. et al Vox Sang. 50 21–25 (1986).

2. Total protein was measured using the Bradford assay (Bradford, M.M. Anal. Biochem. 72 248–254 (1976)).

3. Immobilised ligand concentrations on the gels were determined using picryl sulphonic acid to detect primary amino groups. 0.50 ml of wet settled gel was mixed at room temperature for about 1 hour with 9.5 ml of a 2.5 mg/ml solution of picryl sulphonic acid in saturated aqueous sodium tetraborate. The gel was collected by centrifugation, and the pellet washed several times with water until the supernatant was colourless. Solubilisation of the pellet was achieved by addition of 9.5 ml of 5 M HCl and heating to 75° C. The sample was further diluted (either 20 or 40 fold) with 5 M HCl, and the $OD_{349}$ was taken. A 40 mM solution of ε-amino caproic acid was used as standard. 0.5 ml of this solution was allowed to react with 9.5 ml of the picryl sulphonic acid solution. 0.5 ml of this solution was treated with 9.5 ml of 5 M HCl as for the sample, and the $OD_{349}$ read, diluting the solution with 5 M HCl by 2 if necessary. A picryl sulphonic acid reagent blank was also prepared, and the $OD_{349}$ subtracted from that for the standard, but not for the sample.

For three of the gels which proved insoluble in hot 5 M HCl, namely TETA-Sephacryl S-500, TETA-Fractogel TSK HW55 and TETA-Trisacryl GF 2000, the ligand concentrations were determined by acid/base titration.

4. Specific proteins (fibrinogen, fibronectin and vWF) were analysed by the method of Laurell, C-B (1972) Scand. J. Clin. Invest. 29, Suppl. 124, 21–37.

Buffer solutions

Buffer A : 0.1 M acetate, 0.1 M lysine HCl, 10% (v/v) glycerol, 10 mM $CaCl_2$, pH 5.50.
Buffer B : 0.1 M acetate, 0.1 M lysine HCl pH 5.50.
Buffer C : 0.2 M acetate, 1 mM imidazole, pH 5.50.
Buffer D : as buffer A, but pH set to 5.0.
Buffer E : 0.1 M Bis-Tris, 0.1 M lysine HCl, 10% (v/v) glycerol, 10 mM $CaCl_2$, pH 6.0.
Buffer F : as buffer E, but pH set to 6.5.
Buffer G : 0.1 M Tris, 0.1 M lysine HCl, 10% (v/v) glycerol, 10 mM $CaCl_2$, pH 7.0.
Buffer H : as buffer G, but pH set to 7.9.

All buffers additionally contained 0.02% sodium azide as preservative.

Methods of Preparing Solutions Containing Factor VIII

"Cryoprecipitate" was formed by thawing fresh frozen plasma so that the temperature of the thawing mass was kept at 0°–2° C. Cryoprecipitate was collected from the thawed suspension by centrifugation and dissolved in 20 mM Tris buffer pH 7.0, using 24 ml buffer per kg plasma This solution is called "cryo-solution", and was further purified by cooling the solution to 10° C. and removing the precipitate which formed by centrifugation. The supernatant was adjusted to pH 7.0 and treated with Alhydrogel (2.0% $Al(OH)_3$ manufactured by Superfos, Denmark), at a rate of 5 ml gel per kg original plasma The Alhydrogel was removed by centrifugation, and the supernatant was sterilised by membrane filtration, dispensed into glass vials and lyophilised. This preparation is called "intermediate purity factor VIII concentrate" (IPC) and has an approximate composition, when reconstituted in the original volume of:

| Factor VIII | 5.6 iu/ml |
|---|---|
| Total protein | 21 mg/ml |
| vWF | 12.5 u/ml |
| Fibrinogen | 19 mg/ml |
| Fibronectin | 4.3 mg/ml |

The factor VIII in cryo-solution was alternatively purified by addition of sodium heparin USP to a final concentration of 0.6 to 0.9 mg/ml at a pH of 6.4 to 6.6 and a temperature of 25°-30° C., and removal by centrifugation of the precipitated fibrinogen and fibronectin. This factor VIII-rich supernatant is called "heparin supernatant" and has the following approximate composition:

| Factor VIII | 7.2 iu/ml |
|---|---|
| Total protein | 12.2 mg/ml |
| vWF | 33 u/ml |
| Fibrinogen | 4.5 mg/ml |
| Fibronectin | 1.9 mg/ml |

The factor VIII in cryo-solution was alternatively purified by addition of sodium heparin as described above followed by addition of Alhydrogel at a concentration 2-12% v/v. The heavy precipitate of fibrinogen, fibronectin and Alhydrogel was removed by centrifugation. The resulting factor VIII rich supernatant is called "heparin/Alhydrogel supernatant" and has a composition similar to that of the heparin supernatant except that the vitamin-K dependent clotting factors (e.g. factor II, IX and X) have been depleted.

The factor VIII in heparin supernatant was further purified by addition of glycine and NaCl to final concentrations of 1.48 M and 2.36 M respectively at pH 7.0 and 30° C., and collection of the factor VIII-rich precipitate by centrifugation The precipitate was redissolved in about 1/520 times the original plasma volume of 0.10 M sodium chloride, 0.01 M Tris, 0.01 M sodium citrate, 1.2 mM calcium chloride, 1.5% (w/w) sucrose, pH 6.9 buffer and then desalted using the gel filtration medium Sephadex G-25 into the same buffer.

The factor VIII solution was sterilised by membrane filtration, dispensed into sterile glass vials, lyophilised and heated at 80° C. for 72 h to inactivate viruses. This preparation is called "high purity concentrate" (HPC) and has an approximate composition, when reconstituted in the original volume of:

| Factor VIII | 23.5 iu/ml |
|---|---|
| Total protein | 6.0 mg/ml |
| v/WF | 62.3 u/ml |
| Fibrinogen | 4.6 mg/ml |
| Fibronectin | 0.31 mg/ml |

Column Chromatography

All chromatography was carried out at room temperature and at a flow rate appropriate to the column size. Total protein in the effluent was monitored at 280 nm using an LKB Uvicord High purity concentrate factor VIII samples were dissolved in the appropriate loading buffer, at room temperature or 37° C., and any insoluble material removed by centrifugation prior to loading onto the column. After loading, the column was washed with loading buffer until the $OD_{280}$ was near the baseline. Then protein was eluted either by step or gradient increase in salt concentration. Gradients were formed using 3-channels of a peristaltic pump (Gilson). The position of the eluted factor VIII activity was then determined, and plotted on the $OD_{280}$ trace. The sodium chloride concentrations in the fractions were determined using a conductivity meter and an appropriate calibration curve. Where elution was carried out in a step-wise fashion, a lower concentration was first used to elute bound protein without removing more than about 5% of the loaded factor VIII activity, and then a higher concentration used to remove the factor VIII. Appropriate electrolyte concentrations were determined for each matrix.

EXAMPLE 1

Synthesis Of Separation Media

Using the methods of coupling, ligands and supports described above, the separation media set out below were synthesised.

polyamine Ligand A - Sepharose 4B - ECH coupled
polyamine Ligand B - Sepharose 4B - ECH coupled
polyamine Ligand C - Sepharose 4B - ECH coupled
polyamine Ligand D - Sepharose 4B - ECH coupled
polyamine Ligand E - Sepharose 4B - ECH coupled
polyamine Ligand F - Sepharose 4B - ECH coupled
polyamine Ligand G - Sepharose 4B - ECH coupled
polyamine Ligand H - Sepharose 4B - ECH coupled
polyamine Ligand I - Sepharose 4B - ECH coupled
polyethyleneimine - Sepharose 6B - ECH coupled
polyallylamine - Sepharose 4B - ECH coupled
polyvinylamine - Sepharose 4B - ECH coupled
TETA - Trisacryl GF2000 - CDI coupled
TETA - Sephadex G25 - ECH coupled
TETA - Sephacryl S-500 - CDI coupled
TETA - Fractogel TSK HW 55 - ECH coupled
TETA - Sepharose 6B - ECH coupled
N-methylated TETA - Sepharose 4B - ECH coupled
TETA - Sepharose 4B - BDE coupled
TETA - Sepharose CL-6B - CDI coupled

EXAMPLE 2

TETA-Sepharose 4B ECH coupled, purification of HPC

A 10 ml column (1.6×5.0 cm) of TETA-Sepharose 4B (ECH coupled, 27 μmol/ml ligand concentration) was packed and equilibrated with about 50 ml of buffer A.

A sample of two vials of high purity concentrate (batch 8Y 2278) dissolved in 20 ml of buffer A was loaded onto the column at a flow rate of 60 ml/hr. The column was then washed and eluted sequentially with buffer A (50 ml), buffer A+0.25 M NaCl (100 ml) and finally buffer A+1.0 M NaCl (40 ml). Fractions of 10 ml were collected and pooled according to the changes in salt concentration. Factor VIII activity and total protein amounts were determined in the starting material and the pooled fractions. Results are shown in Table 2.

TABLE 2

|  | Factor VIII (iu) | Total Protein (mg) | Specific Activity (iu/mg) |
|---|---|---|---|
| Starting Sample | 438 (100%) | 73 | 6.0 |
| Unadsorbed | 36 (8%) | — | — |
| 0.25 M NaCl eluate | 7 (1.6%) | — | — |
| 1.00 M NaCl eluate | 296 (68%) | 0.86 | 344 (57 fold) |

EXAMPLE 3

TETA - Sepharose 4B ECH Coupled, purification of heparin supernatant

A 1.0 ml column (0.7×2.6 cm) of TETA-Sepharose 4B (33 μmol/ml, ECH-coupled) was equilibrated with buffer A.

Heparin supernatant (8 volumes) was prepared for chromatography by the addition of a mixture of glycerol (1 volume) 1 M lysine HCl/1 M acetate pH 5.5 (1 volume) and 1 M calcium chloride (0.1 volume). A sample containing approximately 100 iu of factor VIII was loaded onto the column at a flow rate of 10 ml/hr. The column was then washed sequentially with buffer A (10 ml), buffer A+0.20 M NaCl (10 ml) and finally buffer A+1.0 M NaCl (5 ml).

Fraction pools were made as in Example 2, and assayed for factor VIII activity, total protein, vWF, fibronectin and fibrinogen. Results are shown in Table 3.

TABLE 3

| | Factor VIII (iu) | Total Protein (mg) | vWF (u) | Fibronectin (mg) | Fibrinogen (mg) |
|---|---|---|---|---|---|
| Starting sample | 96 | 112 | 342 | 6.5 | 47 |
| Unadsorbed | 1.5 | 104 | 149 | 4.9 | 48 |
| 0.20 M NaCl eluate | 0.9 | 2 | 37 | 1.1 | 0.6 |
| 1.0 M NaCl Eluate | 69 | 0.7 | 39 | 0.2 | 0.3 |

EXAMPLE 4

Sepharose 4B ECH Coupled to 8 polyamine ligands, purification of HPC

Sepharose 4B gels to which a series of 8 different polyamine ligands (Table 1) had been attached by ECH coupling were tested for factor VIII purification using the following method. 10 ml columns were packed (1.6×5.0 cm) and equilibrated with buffer B. Samples were of high purity concentrate, batch 8Y 2278, and were prepared by dissolution of one vial of concentrate in 10 ml of buffer B. The columns were loaded at a flow rate of 60 ml/hr, and then washed with buffer B until the $OD_{280}$ of the effluent was near the baseline. Elution of bound protein was then effected using a linear sodium chloride gradient, generally of total volume 130 ml, in buffer B.

The gradients were 0.0 to 1.0 M in all cases except for compound G, for which the column was first washed with 0.50 M NaCl (40 ml), and then a 0.50 to 1.5 M gradient (130 ml) was used, and compound H for which a 0.0 to 1.3 M (130 ml) gradient was used.

Gradients were formed using 3-channels of a peristaltic pump (Gilson), and fractions of 10 ml were collected. Eluted factor VIII activities, and sodium chloride concentrations (determined using a conductivity meter and an appropriate calibration curve) were plotted against the fraction numbers on the $OD_{280}$ trace. Results are shown in Table 4, in which the column headed "Relative performance" refers to a visual assessment of the separation of the peak of eluted factor VIII activity from the peak of eluted protein.

TABLE 4

| | Ligand | Ligand conc. on Sepharose 4B (μmol/ml) | [NaCl] at which peak Factor VIII eluted (mM) | Relative Performance | Q Value |
|---|---|---|---|---|---|
| 1 | 1,4,8-tri-aza-octane | 30 | 530 | *** | 1.5 |
| 2 | 1,3,7,10-tetra-aza-decane (TETA) | 26 | 590 | *** | 1.5 |
| 3 | 1,4,8,11-tetra-aza-undecane | 29 | 713 | **** | 1.9 |
| 4 | 1,5,8,12-tetra-aza-dodecane | 32 | 655 | *** | 1.6 |
| 5 | 1,5,9,13-tetra-aza-tridecance | 26 | 530 | ** | 1.3 |
| 6 | 1,4,7,10,13-penta-aza-tridecance | Not Determined | 440 | ** | 1.2 |
| 7 | 1,4,8,11,15,18-hexa-aza-octadecane | 32 | 870 | ***** | $^a$2.4 |
| 8 | 1,4,7,10,13,16-hexa-aza-hexadecane | 33 | 580 | *** | $^a$1.6 |

$^a$Q value calculated using assumed $pK_a$ values:
6 nitrogens protonated at pH 5.5 for ligand 7
4 nitrogens protonated at pH 5.5 for ligand 8

From these results it can be seen that there is a good correlation between the calculated Q values and the performance of the ligands. There is also a linear relationship between the Q values and the concentrations of sodium chloride at which the factor VIII peaks are eluted as shown in FIG. 1.

EXAMPLE 5

Using the same method as for the smaller polyamines, Sepharose gels were prepared using three polymeric amino compounds: polyethyleneimine (PEI); polyvinylamine; and polyallylamine. These matrices were tested for factor VIII purification, using the general methods of Examples 2 and 4.

(i) PEI-Sepharose 6B ECH Coupled, purification of HPC

A column of 2.0 ml (1.6×1.0 cm) PEI-Sepharose 6B (ECH-coupled) was equilibrated with buffer A+0.5 M NaCl. Two vials of high purity concentrate (batch 8Y 2278) were dissolved in 20 ml of the same buffer and loaded onto the column at a flow rate of 18 ml/hr. The column was sequentially eluted with a short (28 ml) 0.5 to 0.7 M NaCl gradient, and then a 0.7 to 2.0 M NaCl gradient (25 ml). Results are shown in Table 5.

TABLE 5

|  | Factor VIII (iu) | Total Protein (mg) | Specific Activity (iu/mg) |
|---|---|---|---|
| Starting Sample | 454 (100%) | 152 | 2.97 |
| Unadsorbed | 36 (8%) | 118 | 0.30 |
| 0.5 to 0.7 M NaCl eluate | 3 (0.7%) | 3.3 | 0.92 |
| 0.7 to 2.0 M NaCl eluate | 374 (82%) | 0.76 | 492 (166 fold) |

(ii) Polyallylamine-Sepharose 4B ECH coupled, purification of HPC

This gel was tested in a similar manner to method in Example 5(i). Buffer A+0.90 M NaCl was used to prepare the sample and equilibrate the column, and after loading of the sample, the column was washed with loading buffer and then bound proteins were eluted with a 0.9 to 2.3 M NaCl gradient. 6% of the loaded factor VIII was unadsorbed, and 82% was recovered in the eluate, with a purification of about 50-fold.

(iii) Polyvinylamine-Sepharose 4B ECH coupled, purification of HPC

This gel was tested in a similar manner to the method in Example 5(ii), except that the initial NaCl concentration was 1.0 M, and a 1.0 to 3.5 M NaCl gradient was used for elution. 11% of the factor VIII remained unbound, and 66% was recovered in the eluate, again with a purification of about 50-fold.

EXAMPLE 6
TETA coupled to various supports

TETA may also be attached to supports other than Sepharose, and the matrices can be used for factor VIII purification.

(i) TETA-Trisacryl GF 2000 CDI coupled, purification of HPC

Example 2 was repeated, but using Trisacryl GF 2000 as the support to which TETA had been attached at a level of 57 $\mu$mol/ml by the CDI method. 53% of the loaded factor VIII was eluted with an 80-fold increase in specific activity.

(ii) TETA-Sephadex G25 ECH coupled, purification of HPC

Example 2 was repeated, but using Sephadex G25 as the support to which TETA had been attached at a level of 89 $\mu$mol/ml by the ECH method. The column was equilibrated with buffer B, and a sample of 1 vial of high purity concentrate dissolved in 10 ml of buffer B was loaded. The column was washed with loading buffer and eluted with buffer +0.30 M NaCl. 47% of the applied factor VIII was recovered with an increase in specific activity of about 50-fold.

(iii) TETA-Sephacryl S-500 CDI coupled, purification of HPC

A 2.0 ml (1.0×2.5 cm) column of TETA-Sephacryl S-500, which had been prepared using the CDI method and had a substitution level of 28 $\mu$mol/ml, was equilibrated with buffer A. One vial of high purity concentrate was prepared, loaded and eluted as described in Example 2, except that 0.30 M NaCl was used in the wash buffer. 99% of the loaded factor VIII activity was recovered in the eluate with an increase in specific activity of at least 50-fold.

(iv) TETA-Fractogel TSK HW-55. ECH coupled, purification of heparin supernatant

A 2.0 ml (1.0×2.5 cm) column of TETA-Fractogel TSK HW-55, which had been prepared using the ECH method and had a substitution level of 57 $\mu$mol/ml, was equilibrated with buffer A. A sample of heparin supernatant containing 166 iu of Factor VIII was prepared according to the method in Example 3, and loaded onto the column. Unadsorbed protein was removed using buffer A, a wash was performed using buffer A+0.25 M NaCl, and buffer A+1.0 M NaCl was used to elute the Factor VIII. 70% of the loaded Factor VIII activity was recovered in the eluate, with a purification of 115-fold.

EXAMPLE 7
Purification of factor VIII from different starting materials

Factor VIII-containing starting materials other than those described in the above examples can also be used.

(i) IPC purified on TETA-Sepharose 4B ECH coupled

One vial of intermediate purity concentrate was dissolved in 30 ml of buffer B, and chromatographed as described in Example 2, except that buffer B was used in place of buffer A, and 0.30 M NaCl was used for the low salt wash. Results are shown in Table 6.

TABLE 6

|  | Factor VIII (iu) | Total Protein (mg) | Specific Activity (iu/mg) |
|---|---|---|---|
| Starting Sample | 208 (100%) | 1017 | 0.21 |
| Unadsorbed | 23 (11%) | — | — |
| 0.30 M NaCl eluate | 10 (5%) | — | — |
| 1.00 M NaCl eluate | 100 (48%) | 1.2 | 84 (400-fold) |

(ii) Plasma purified on TETA-Sepharose 6B 20 ml of plasma was buffer exchanged using a column (2.0×18.0 cm) of Sephadex G-25 into 75 mM NaCl in water, pH 7.4. The pooled eluate (32 ml) was mixed simultaneously with 1.0 M acetate, 1.0 M lysine HCl, pH 5.50 (4.0 ml), glycerol (4.0 ml) and 1 M $CaCl_2$ (0.4 ml). The pH of the mixture was adjusted to 5.50 using 1.0 M acetate, pH 5.0. A sample of TETA-Sepharose 6B (ECH coupled, ligand concentration 48 $\mu$mol/ml) was washed with five volumes each of 0.1 M NaOH, water, 0.1 M HCl and Buffer A. 1.0 g of the gel was mixed with 39 ml of the adjusted plasma for 1 hour, then collected by centrifugation (150 g, 15 minutes) and poured into a column. The column was washed with buffer A (6 ml) and then eluted with buffer A+1.0 M NaCl (10 ml). The results are shown in Table 7.

TABLE 7

|  | Factor VIII (iu) | Total Protein (mg) | Specific Activity (iu/mg) |
|---|---|---|---|
| Plasma | 13.5 (100%) | 2025 | 0.0067 |
| Adjusted plasma | 10.1 (75%) | 1984 | 0.0052 |
| Eluate | 11.4 (85%) | 11.4 | 1.00 (150-fold) |

(iii) Prothrombin-depleted plasma purified on TETA-Sepharose 6B

A sample of 1.5 g DEAE Sephadex A-50 was pre-swollen in 100 ml 75 mM NaCl. 1.66 ml of this suspension was mixed for 2 hours with 50 ml of freshly thawed plasma. The DEAE-Sephadex was removed by centrifugation, and 22 ml of the supernatant was diluted with an equal volume of water. After adjustment of its pH to 5.5, the plasma preparation was adsorbed and chromatographed with 1.0 g of TETA-Sepharose 6B as described in Example 7(ii), except that the column was additionally washed with 0.2 M NaCl in Buffer A prior to elution. 75% of the factor VIII activity in the adjusted plasma was recovered in the eluate, with a specific activity of 2.4 iu/mg. Measurement of prothrombin indicated that 98.5% was removed by treatment of the plasma with DEAE-Sephadex, and that only 0.4% of the original plasma prothrombin was recovered in the eluate from the TETA-Sepharose.

(iv) Heparin/Alhydrogel supernatant purified on TETA-Sepharose 4B

A sample of heparin/alhydrogel supernatant was treated with 0.3% tri-n-butyl phosphate (TNBP) and 1% Tween 80 at room temperature overnight, and then the sample was prepared for chromatography as described in Example 3. 23 ml of this solution was then loaded onto a column of 1.0 ml of TETA-Sepharose 4B (ECH coupled 32 μmol/ml TETA) which had been equilibrated with buffer A. The column was developed as described in Example 2, except that the low salt wash contained 0.20 M NaCl. Results are shown in Table 8.

TABLE 8

| | Factor VIII (iu) | Total Protein (mg) | vWF (u) | Fibronectin (mg) | Fibrinogen (mg) |
|---|---|---|---|---|---|
| Starting sample | 133 | 224 | 273 | 16.6 | 20.1 |
| Combined unbound and 0.2 M NaCl eluate | 9.7 | 178 | 284 | 12.6 | 15.8 |
| 1.0 M NaCl Eluate | 88 | 1.9 | 37 | 0.27 | 0.13 |

EXAMPLES 8 and 9

It is possible, by means of transition metal binding and chemical reaction to alter the chromatographic properties towards factor VIII of a polyamine ligand such as compound 2 (TETA).

EXAMPLE 8

TETA-Sepharose 4B ECH coupled, loaded with $Cu^{II}$, purification of IPC

A sample of TETA-Sepharose 4B was packed into a column (10 ml) in the usual manner but using water rather than buffer and then loaded with $Cu^{ii}$ ions by passage of a 10 mg/ml solution of $CuCl_2$ in water. Saturation of the matrix with $Cu^{II}$ ions was readily observable, since the matrix became brilliant blue. The column was washed with water, 100 mM imidazole buffer, pH 7.0, containing 1.0 M NaCl and finally with buffer C. A sample of intermediate purity concentrate was prepared in buffer C, and loaded onto the column. The column was washed with buffer, and bound proteins eluted with a 0.0 to 1.0 M NaCl gradient. Peak factor VIII activity was eluted at a concentration of 0.38 M NaCl, and the overall recovery was 61%.

EXAMPLE 9

N-methylated TETA-Sepharose 4B ECH coupled, purification of HPC

A sample of TETA Sepharose 4B, which had been prepared as described above using ECH as coupling agent was reacted with methyl iodide under conditions which would be expected to fully methylate all the nitrogens giving a ligand structure:

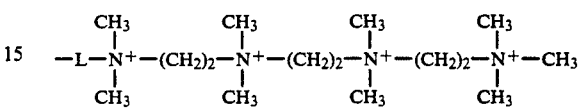

20 ml of gel was transferred to an environment of methanol, and suspended in 80 ml of the same solvent. 4.0 ml of methyl iodide and 4.0 g of potassium hydrogen carbonate were added, and the mixture was agitated at 40° C. for 3 days. The gel was returned to an aqueous environment and tested for its ability to (a) bind $Cu^{II}$ ions (b) react with picryl sulphonic acid, both of which proved to be negative.

A column of the modified gel was tested by loading a sample of high purity concentrate in buffer B, and washing the column with further buffer B, buffer B+0.1 M NaCl and finally buffer B+0.2 M NaCl. 46% of the loaded activity was recovered in the 0.2 M NaCl fraction, with a purity similar to that obtained with unmodified TETA under appropriate conditions.

EXAMPLE 10

Use of a matrix containing a spacer between the ligand (TETA) and the gel

TETA-Sepharose 4B was prepared using 1,4-butanediol-diglycidyl ether as coupling agent as described above. The amount of coupled TETA was 18.0 μmol/ml. The gel was tested for factor VIII purification using the method of Example 4. Results showed that both the factor VIII and total protein were less tightly bound than when ECH was used as the coupling agent in the preparation of the gel. Peak factor VIII was eluted at 165 mM NaCl, and the overall recovery was 89%.

EXAMPLE 11

Variation of the pH for Chromatography

Buffers of different pH, between 5.0 and 7.9, were used for chromatography. 2.0 ml (1.0×2.5 cm) columns of TETA-Sepharose CL-6B, which had been prepared using the CDI method and had a substitution level of 39 μmol/ml, were packed and equilibrated with the appropriate buffer for the particular experiment. One vial of high purity concentrate (batch 8Y 3492) was reconstituted in 10 ml of the appropriate buffer, and loaded onto the column at a flow rate of 24 ml/hr. Unbound protein was removed using further quantities of loading buffer, and a 0.25 M NaCl wash was performed followed by elution with 1.0 M NaCl. The percentages of loaded factor VIII remaining unbound and the percentages recovered in the 1.0 M NaCl eluate are shown in Table 9. Of the pHs which were tested, pH 5.5 is optimal for recovery of factor VIII in the 1.0 M NaCl eluate and minimisation of losses due to its remaining unbound.

TABLE 9

| Buffer | pH | Factor VIII Unbound (%) | Factor VIII Eluted (%) | Specific Activity of Eluates iu/mg |
| --- | --- | --- | --- | --- |
| D | 5.0 | 24 | 17 | 295 |
| A | 5.5 | 19 | 42 | 355 |
| E | 6.0 | 33 | 38 | 306 |
| F | 6.5 | 37 | 17 | 117 |
| G | 7.0 | 42 | 10 | 164 |
| H | 7.9 | 49 | 10 | 350 |

EXAMPLE 12

Use of Salts other than NaCl for Elution

Several experiments were carried out as described in Example 6(iii). After the 0.30 M NaCl wash, bound factor VIII was recovered using buffer A and the particular salt being tested. The recoveries of factor VIII are shown in Table 10.

TABLE 10

| Salt Eluate | Concentration (M) | Factor VIII Eluate (%) | Specific Activity Recovered in iu/mg of |
| --- | --- | --- | --- |
| $(NH_4)Cl$ | 1.0 | 88 | 114 |
| $Na_2SO_4$ | 0.33 | 12 | 20 |
| $(NH_4)_2SO_4$ | 0.20 | 63 | 56 |
| Tri-sodium citrate + $CaCl_2$ | + 0.167 0.020 | 33 | 162 |
| NaCl | 1.0 | 75 | 561 |

Thus although salts other than NaCl may be used for elution of factor VIII, the recovery achieved in the eluate depends on the identity of the salt.

We claim:

1. A separation medium for use in protein separation comprising a water-insoluble matrix carrying a plurality of polyamine groupings, said polyamine groupings each having at least 3 basic nitrogen atoms, said basic nitrogen atoms being separated from each other by a chain of at least two intervening carbon atoms, there being a total of 5 such intervening carbon atoms when there is a total of three nitrogen atoms in each polyamine grouping.

2. A separation medium as claimed in claim 1 wherein the matrix is an organic matrix.

3. A separation medium as claimed in claim 1 wherein each polyamine grouping has at least four nitrogen atoms.

4. A separation medium as claimed in claim 1 wherein each polyamine grouping is a straight chain, branched chain, monocyclic or polycyclic polyamine grouping.

5. A separation medium as claimed in claim 1 wherein the polyamine groupings attached to the matrix are different from each other.

6. A separation medium as claimed in claim 1 wherein the intervening carbon atoms between pairs of nitrogen atoms form an alkylene or cycloalkylene grouping.

7. A separation medium as claim in claim 1 wherein the polyamine groupings are linear polyalkylene polyamine groupings having 2 or 3 carbon atoms in the alkylene groupings.

8. A separation medium as claimed in claim 1 wherein the polyamine groupings are triethylenetetramine.

9. A separation medium as claimed in claim 1 wherein the water-insoluble matrix is a hydrophilic polymeric substance.

10. A separation medium as claimed in claim 1 wherein the matrix material is agarose, cellulose, dextran, macroporous silica or polyacrylamide.

11. A separation medium as claimed in claim 1 wherein the polyamine groupings are coupled to the matrix using a di-functional coupling reagent having 1-10 carbon atoms.

12. A separation medium as claimed in claim 11 wherein the coupling reagent is epichlorohydrin, carbonyldiimidazole or 1,4-butanediol diglycidyl ether.

13. A separation medium as claimed in claim 1, wherein said medium is an agarose gel coupled via epichlorohydrin to triethylenetetramine.

14. A method of at least partially purifying factor VIII comprising loading a factor VIII-containing sample onto the separation medium claimed in claim 1, washing, and eluting a fraction enriched in factor VIII.

15. A method as claimed in claim 14 wherein the factor VIII-containing material is whole plasma, cryoprecipitate, or partially purified factor VIII.

16. A method as claimed in claim 14 executed by column chromatography.

17. A method as claimed in claim 14 wherein the factor VIII-containing material is loaded onto the separation medium in the presence of a loading buffer solution at a pH between 5.0 and 8.0.

18. A method as claimed in claim 17 wherein the pH is 5.5.

19. A method as claimed in claim 17 wherein the loading buffer solution is at an ionic strength of 0.2 M.

20. A method as claimed in claim 14 wherein elution is effected with an increasing concentration of electrolyte.

21. A method as claimed in claim 20 wherein the electrolyte concentration varies from 0.2 to 4.0 M.

22. The separation medium as claimed in any one of claim 1 to 7, wherein the polyamine groupings are polyalkyleneamine groupings wherein two nitrogen atoms are joined by two sets of intervening carbon atoms to form a cyclic grouping.

23. The separation medium as claimed in claim 22, wherein the polyamine groupings are of the formula:

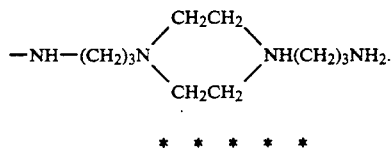

* * * * *